(12) United States Patent
Glenn et al.

(10) Patent No.: US 9,974,946 B2
(45) Date of Patent: May 22, 2018

(54) INFLATABLE INTRAVASCULAR ELECTRODE SUPPORTS FOR NEUROMODULATION

(71) Applicant: NeuroTronik IP Holding (Jersey) Limited, St. Helier (JE)

(72) Inventors: Richard A Glenn, Chapel Hill, NC (US); Stephen C Purcell, Carrboro, NC (US)

( * ) Notice: Subject to any disclaimer, the term of this patent is extended or adjusted under 35 U.S.C. 154(b) by 0 days. days.

(21) Appl. No.: 14/681,036

(22) Filed: Apr. 7, 2015

(65) Prior Publication Data

US 2016/0296747 A1    Oct. 13, 2016

(51) Int. Cl.
*A61N 1/05* (2006.01)

(52) U.S. Cl.
CPC .......... *A61N 1/0551* (2013.01); *A61N 1/0558* (2013.01)

(58) Field of Classification Search
CPC ....... A61N 1/05; A61N 1/0551; A61N 1/0558
USPC ..................................... 607/2, 116
See application file for complete search history.

(56) References Cited

U.S. PATENT DOCUMENTS

| | | | | |
|---|---|---|---|---|
| 4,762,130 A * | 8/1988 | Fogarty | ............ | A61B 17/22032 604/103.07 |
| 5,273,052 A * | 12/1993 | Kraus | ............. | A61M 25/09041 600/585 |
| 5,324,259 A * | 6/1994 | Taylor | ................. | A61M 25/104 604/103.1 |
| 5,749,890 A * | 5/1998 | Shaknovich | ............ | A61F 2/958 128/898 |
| 6,004,269 A * | 12/1999 | Crowley | ............... | A61B 8/4461 600/374 |
| 6,165,127 A * | 12/2000 | Crowley | ................ | A61B 5/416 600/439 |
| 6,491,619 B1 * | 12/2002 | Trauthen | ............... | A61K 9/1641 257/E21.058 |
| 6,500,147 B2 * | 12/2002 | Omaleki | ............... | A61M 25/09 604/103.09 |
| 6,645,135 B1 * | 11/2003 | Bhat | ..................... | A61M 25/10 600/3 |
| 6,986,778 B2 * | 1/2006 | Zadno-Azizi | .... | A61B 17/12022 604/107 |
| 7,001,420 B2 * | 2/2006 | Speck | .................. | A61M 25/005 604/103.09 |
| 7,122,019 B1 * | 10/2006 | Kesten | ................... | A61M 25/10 600/16 |
| 7,241,273 B2 * | 7/2007 | Maguire | ............... | A61M 25/10 604/104 |
| 7,329,236 B2 * | 2/2008 | Kesten | .............. | A61M 25/1002 604/96.01 |
| 7,335,192 B2 * | 2/2008 | Keren | ................... | A61M 1/101 604/101.03 |
| 7,435,257 B2 * | 10/2008 | Lashinski | .......... | A61B 17/0644 623/2.11 |
| 7,481,803 B2 * | 1/2009 | Kesten | ................... | A61K 31/55 604/507 |

(Continued)

*Primary Examiner* — Christopher A Flory (57) ABSTRACT

An intravascular catheter is positionable within a blood vessel for use in transvenous stimulation of targets external to the wall of the blood vessel. The catheter includes a catheter body, a support at the distal end of the catheter body, and a plurality of electrodes carried by the support. At least a portion of the support being inflatable within the blood vessel to bias at least a portion of the plurality of electrodes into contact with the blood vessel wall.

8 Claims, 8 Drawing Sheets

(56) References Cited

U.S. PATENT DOCUMENTS

| | | | | |
|---|---|---|---|---|
| 7,556,645 B2* | 7/2009 | Lashinski | A61B 17/0644 | 623/2.1 |
| 7,563,247 B2* | 7/2009 | Maguire | A61M 25/10 | 604/103.01 |
| 8,043,257 B2* | 10/2011 | Nguyen | A61M 25/0084 | 604/101.01 |
| 8,075,519 B2* | 12/2011 | Min | A61M 25/0084 | 604/104 |
| 8,377,033 B2* | 2/2013 | Basu | A61B 17/12045 | 600/37 |
| 8,568,355 B2* | 10/2013 | Min | A61M 25/0084 | 604/104 |
| 8,652,098 B2* | 2/2014 | Haslinger | A61M 25/0108 | 604/103.1 |
| 8,740,895 B2* | 6/2014 | Mayse | A61B 18/1492 | 606/16 |
| 8,777,943 B2* | 7/2014 | Mayse | A61B 18/1492 | 606/41 |
| 8,858,612 B2* | 10/2014 | Ben-Muvhar | A61F 2/91 | 623/1.11 |
| 8,932,289 B2* | 1/2015 | Mayse | A61B 18/1492 | 606/41 |
| 8,934,956 B2* | 1/2015 | Glenn | A61B 5/0422 | 600/374 |
| 9,005,195 B2* | 4/2015 | Mayse | A61B 18/1492 | 606/41 |
| 9,017,324 B2* | 4/2015 | Mayse | A61B 18/1492 | 606/41 |
| 9,067,071 B2* | 6/2015 | Sanders | A61N 1/36053 | |
| 9,084,609 B2* | 7/2015 | Smith | A61B 18/1492 | |
| 2002/0029046 A1 | 3/2002 | Lorentzen Cornelius | A61F 2/958 | 606/108 |
| 2002/0038103 A1* | 3/2002 | Estrada | A61M 25/09 | 604/103.09 |
| 2002/0065507 A1* | 5/2002 | Zadno-Azizi | A61B 17/12022 | 604/509 |
| 2003/0060802 A1* | 3/2003 | Omaleki | A61M 25/09 | 604/528 |
| 2003/0074039 A1* | 4/2003 | Puskas | A61N 1/0517 | 607/118 |
| 2003/0153871 A1* | 8/2003 | Kumazaki | A61M 25/1011 | 604/101.04 |
| 2003/0166990 A1* | 9/2003 | Trauthen | A61K 9/1641 | 600/3 |
| 2004/0133263 A1* | 7/2004 | Dusbabek | A61F 2/958 | 623/1.11 |
| 2005/0154440 A1* | 7/2005 | Limon | A61F 2/958 | 623/1.11 |
| 2005/0245866 A1* | 11/2005 | Azizi | A61B 17/12022 | 604/96.01 |
| 2006/0020333 A1* | 1/2006 | Lashinski | A61B 17/0644 | 623/2.11 |
| 2006/0020334 A1* | 1/2006 | Lashinski | A61B 17/0644 | 623/2.11 |
| 2006/0025854 A1* | 2/2006 | Lashinski | A61B 17/0644 | 623/1.25 |
| 2006/0025855 A1* | 2/2006 | Lashinski | A61B 17/0644 | 623/2.1 |
| 2006/0200191 A1* | 9/2006 | Zadno-Azizi | A61B 17/12045 | 606/200 |
| 2006/0265000 A1* | 11/2006 | Azizi | A61B 17/12022 | 606/200 |
| 2006/0287703 A1* | 12/2006 | Oepen | A61F 2/954 | 623/1.11 |
| 2007/0083239 A1* | 4/2007 | Demarais | A61N 1/327 | 607/2 |
| 2007/0255379 A1* | 11/2007 | Williams | A61M 5/14276 | 607/120 |
| 2008/0051705 A1* | 2/2008 | Von Oepen | A61F 2/954 | 604/101.01 |
| 2008/0139897 A1* | 6/2008 | Ainsworth | A61B 5/0084 | 600/300 |
| 2008/0200980 A1* | 8/2008 | Robin | A61F 2/2418 | 623/2.11 |
| 2008/0208307 A1* | 8/2008 | Ben-Muvhar | A61F 2/91 | 623/1.11 |
| 2008/0208329 A1* | 8/2008 | Bishop | A61B 17/10 | 623/2.11 |
| 2008/0243233 A1* | 10/2008 | Ben-Muvhar | A61F 2/954 | 623/1.35 |
| 2008/0249464 A1* | 10/2008 | Spencer | A61M 25/1002 | 604/103 |
| 2009/0088836 A1* | 4/2009 | Bishop | A61F 2/2418 | 623/2.1 |
| 2009/0204068 A1* | 8/2009 | Nguyen | A61M 25/0084 | 604/101.01 |
| 2009/0247933 A1* | 10/2009 | Maor | A61B 18/1492 | 604/20 |
| 2009/0248012 A1* | 10/2009 | Maor | A61B 18/1492 | 606/41 |
| 2010/0023088 A1* | 1/2010 | Stack | A61N 1/0558 | 607/44 |
| 2010/0145265 A1* | 6/2010 | Min | A61M 25/0084 | 604/95.03 |
| 2011/0106072 A1* | 5/2011 | Sundquist | A61B 18/1492 | 606/41 |
| 2011/0152912 A1* | 6/2011 | Spencer | A61M 25/1002 | 606/191 |
| 2011/0160846 A1* | 6/2011 | Bishop | A61F 2/2418 | 623/2.11 |
| 2011/0166648 A1* | 7/2011 | Robin | A61F 2/2418 | 623/2.1 |
| 2011/0213460 A1* | 9/2011 | Lashinski | A61B 17/0644 | 623/2.18 |
| 2012/0022629 A1* | 1/2012 | Perera | A61F 2/2418 | 623/1.11 |
| 2012/0029509 A1* | 2/2012 | Smith | A61B 18/1492 | 606/41 |
| 2012/0059355 A1* | 3/2012 | Basu | A61B 17/12045 | 604/508 |
| 2012/0143139 A1* | 6/2012 | Min | A61M 25/0084 | 604/174 |
| 2012/0143179 A1* | 6/2012 | Avitall | A61B 18/1492 | 606/33 |
| 2013/0041458 A1* | 2/2013 | Lashinski | A61B 17/0644 | 623/2.1 |
| 2013/0060318 A1* | 3/2013 | Hassan | A61M 25/09 | 623/1.11 |
| 2013/0085493 A1* | 4/2013 | Bloom | A61B 18/1492 | 606/41 |
| 2013/0150693 A1* | 6/2013 | D'Angelo | A61B 5/036 | 600/373 |
| 2013/0281813 A1* | 10/2013 | Markowitz | A61B 5/0422 | 600/382 |
| 2013/0289556 A1* | 10/2013 | Mayse | A61B 18/1492 | 606/33 |
| 2014/0018723 A1* | 1/2014 | Deem | A61B 18/1492 | 604/21 |
| 2014/0121603 A1* | 5/2014 | Min | A61M 25/0084 | 604/164.03 |
| 2014/0163551 A1* | 6/2014 | Maor | A61B 18/1492 | 606/41 |
| 2014/0309579 A1* | 10/2014 | Rubinsky | A61B 18/1492 | 604/21 |
| 2015/0088239 A1* | 3/2015 | Ben-Muvhar | A61F 2/91 | 623/1.3 |
| 2015/0133892 A1* | 5/2015 | Joe | A61M 25/1018 | 604/509 |
| 2015/0174379 A1* | 6/2015 | Bagaoisan | A61M 25/003 | 604/509 |
| 2015/0196739 A1* | 7/2015 | Simpson | A61M 25/0009 | 604/103 |
| 2015/0238729 A1* | 8/2015 | Jenson | A61F 2/95 | 604/510 |

(56) References Cited

U.S. PATENT DOCUMENTS

2015/0320472 A1* 11/2015 Ghaffari ................. A61B 5/036
                                                        606/21
2016/0008059 A1*  1/2016 Prutchi .............. A61B 18/1492
                                                        606/41
2016/0128767 A1*  5/2016 Azamian ............ A61B 18/1492
                                                        606/41

* cited by examiner

INFLATABLE INTRAVASCULAR ELECTRODE SUPPORTS FOR NEUROMODULATION

TECHNICAL FIELD OF THE INVENTION

The present application generally relates to intravascular electrode arrays for use in neuromodulation. More particularly, the application relates to inflatable supports used to position and bias the intravascular electrodes against the interior wall of a blood vessel.

BACKGROUND

Prior applications filed by an entity engaged in joint research with the owner of the present application describe neuromodulation methods using electrodes positioned in a blood vessel. The electrodes disposed inside the blood vessel are energized to stimulate or otherwise modulate nerve fibers or other nervous system targets located outside the blood vessel. Those prior applications include U.S. Publication No. 2007/0255379, entitled Intravascular Device for Neuromodulation, U.S. 2010/0023088, entitled System and Method for Transvascularly Stimulating Contents of the Carotid Sheath, U.S. application Ser. No. 13/281,399, entitled Intravascular Electrodes and Anchoring Devices for Transvascular Stimulation, International Application PCT/US12/35712, entitled Neuromodulation Systems and Methods for Treating Acute Heart Failure Syndromes, and U.S. application Ser. No. 13/547,031 entitled System and Method for Acute Neuromodulation, filed Jul. 11, 2012. Each of these applications is fully incorporated herein by reference. The latter application describes a system which may be used for hemodynamic control in the acute hospital care setting, by transvascularly directing therapeutic stimulus to parasympathetic nerves and/or sympathetic cardiac nerves using an electrode array positioned in the superior vena cava (SVC).

DETAILED DESCRIPTION

The present application describes intravascular electrode supports having inflatable components. The described support structures may be used in a system for transvascularly delivering electrical therapy to parasympathetic and/or sympathetic nerve fibers using electrodes on a single electrode carrying member positioned in the SVC, e.g. in accordance with systems and methods of the type disclosed in U.S. application Ser. No. 13/547,031 entitled System and Method for Acute Neuromodulation, filed Jul. 11, 2012. However, the disclosed concepts are equally suitable for use in other clinical applications, including those that deliver stimulus from electrodes disposed within other vessels, those where electrodes on the electrode carrying member deliver electrical therapy to only a single type of nerve fiber, and those used to delivery energy for other purposes such as cardiac rhythm management.

Beneficial features of the disclosed supports include their ability to firmly bias the electrodes against the vessel wall so as to capture target nerves through the vessel wall with efficient stimulation energies, to sufficiently anchor the electrode array within the blood vessel to prevent its migration during treatment, to insulate the regions of the electrode that do not contact the vessel wall so as to avoid collateral stimulation through the blood pool, to be collapsed into a low-profile collapsed position for ready passage (e.g. within a sheath) through the vasculature to the target site, to be readily removed from the blood vessel once therapy has been completed, and to maintain a relatively low profile within the vasculature so as to minimize obstruction to blood flow.

In general, the electrode arrays and associated supports may be elements of a catheter that includes a catheter body, the support structure on a distal portion of the catheter body, and the electrode array on the support structure. As disclosed in the prior applications, electrodes in the electrode array are electrically coupled to a neurostimulator that energizes the electrodes using stimulation parameters selected to capture the target nerve fibers and to achieve the desired patient effect. The disclosed embodiments may include arrays of multiple electrodes or electrode pairs so as to give the user (or an automated mapping feature of a neuromodulation system) a variety of electrodes to select between when choosing the optimal electrode or electrode combination to deliver the intended therapy.

The illustrated electrode supports are designed to bias arrays of multiple electrodes in contact with the surrounding vascular wall—such that when energy from an associated neuromodulation system energizes the electrodes, target nerve fibers outside the blood vessel are captured. The embodiments are designed to position the electrodes in positions suitable for delivering electrical therapy to the target fibers from the intended position of the array within the vasculature.

Figure 1A:
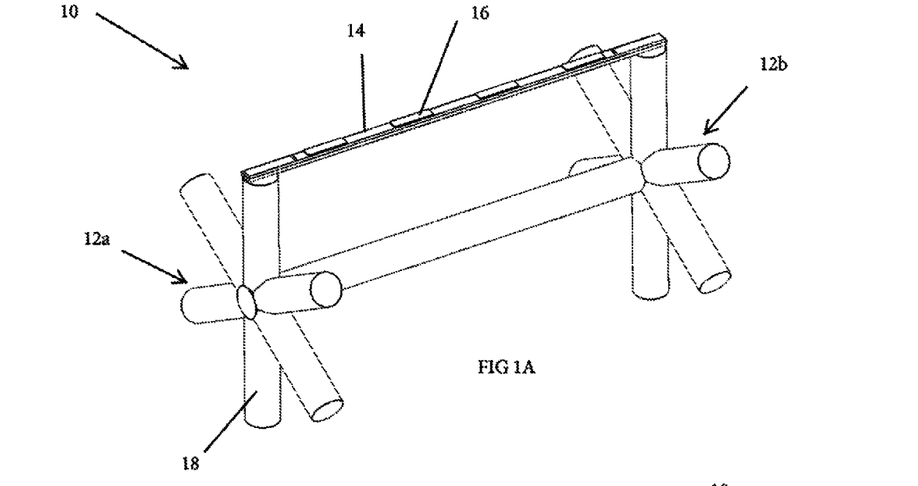
FIG. 1A is a perspective view of a first embodiment of an electrode support.
Figure 1B:
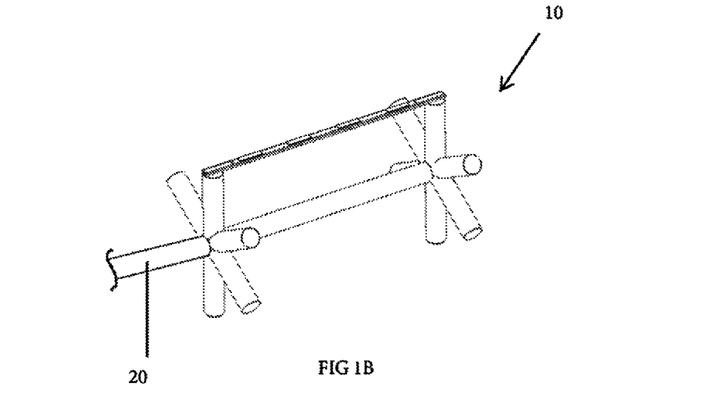
FIG. 1B is a perspective view of the electrode support of FIG. 1A on a distal end of a catheter body.

FIGS. 1A and 1B show a first embodiment of an electrode support 10. Support 10 includes proximal and distal inflatable member 12a, 12b and a plurality of electrode-carrying struts 14 (only one is shown in FIGS. 1A and 1B). Each electrode-carrying strut has a proximal end connected to the proximal inflatable member 12a and a distal end connected to the distal inflatable member 12b. Each electrode carrying strut 14 has at least one, and preferably a plurality of, electrodes 16 disposed thereon.

The proximal and distal inflatable members 12a, 12b may take a variety of forms. Shapes that minimize obstruction to blood flow are particularly desirable. In the FIG. 1A embodiment, these members take the form of spoked members, each having a plurality of spokes 18 extending radially from a hub. In this embodiment, each electrode-carrying strut extends between the free end of a spoke 18 on the proximal inflatable member 12a and that of a spoke 18 on the distal inflatable member. In use, the proximal and distal inflatable members 12a, 12b remain in their deflated state for introduction into the vasculature (within a sheath, for example) and for intravascular passage to target site for electrode deployment. Once at the target site, the inflatable members 12a, 12b are inflated to bias the electrode-carrying struts 14 against the vascular wall, thereby placing the electrodes in firm contact with the wall.

The circumferential cross-sectional shape of each spoke may be circular as shown. In other embodiments, this shape may be chose to minimize obstruction to the flow of blood through the vessel. For example, the shape might be oval or that similar to starlings used to construct in-water piers supporting bridges.

FIGS. 1A and 1B show that the electrode-carrying struts 14 may extend in a longitudinal direction, such that the struts are parallel to one another, by having each strut extend between longitudinally-aligned pairs of the spokes 18. In other embodiments, each strut might have its proximal and distal ends circumferentially off-set from one other to form a helical arrangement. The number of struts may be equal to, or fewer than, the number of proximal-distal spoke pairs.

In some embodiments, the material forming the struts 14 may have a shape set or shape memory that aids in biasing the circumferentially-outward facing surfaces (and thus the electrodes) against the vessel wall. The struts 14 utilize materials or coatings that allow the electrodes' active surfaces (those intended to be placed against the vascular wall) to be exposed, but that insulate the remainder of each electrode's surface(s) against loss of stimulation energy into the blood pool. In some embodiments, the struts 14 may be formed of an insulative substrate such as a polymer (including silicone, polyurethanes, polyimide, and copolymers) or a plastic. The electrodes can be constructed onto the strut substrate using a variety of manufacturing techniques, including subtractive manufacturing processes (such as mechanical removal by machining or laser cutting), additive processes (such as laser sintering, deposition processes, conductor overmolding), or combinations (such as printed circuit technology with additive plating). In some embodiments, the struts and electrodes may be flex circuit or printed circuit elements.

Referring to FIG. 1B, the support 10 is positioned on a catheter body 20. The catheter body 20 may include one or more inflation lumen fluidly coupled to the inflatable members 12a, 12b, or separate inflation tube(s) may extend external to the catheter body 20. In either case, inflation medium (gas, saline) is passed through the inflation lumen or tubes to inflate the inflatable members 12a, 12b. Although the catheter body is shown extending from the hub of the inflatable member 12a, it might instead extend from a free end of a spoke 18 so that the catheter body will extend along the wall of the blood vessel (rather than more centrally within the vessel lumen) when the electrode support is anchored at the target site.

The members 12a, 12b may be separately inflatable or simultaneously inflatable.

A shaft 22 extends between the proximal and distal inflatable members 12a, 12b. The shaft may be an inflatable or non-inflatable member. If inflatable, it may be fluidly coupled to the proximal and distal inflatable members 12a, 12b so that all three members 12a, 12b, 22 may be inflated from a common inflation lumen. In the drawing, the shaft is shown extending between the hubs of the inflatable members 12a, 12b, although in other embodiments it might extend between other parts of the members 12a, 12b, including the longitudinally aligned ends of a pair of the spokes 18. In some embodiments, one of the electrode-carrying struts 14 might also comprise the shaft 22.

In another variation of the first embodiment, the electrode-carrying struts 14 may be eliminated, and instead the electrodes may be positioned at the free ends of the spokes 18. In this variation, there may be additional spoked inflatable members used in combination with the proximal and distal inflatable members 12a, 12b. For example, four spoked inflatable members (including the proximal and distal members 12a, 12b), each with electrodes at the free ends of the plurality of the spokes, might be carried by a common flexible shaft 22 (which, as discussed above, may or may not be inflatable).

Figure 2:
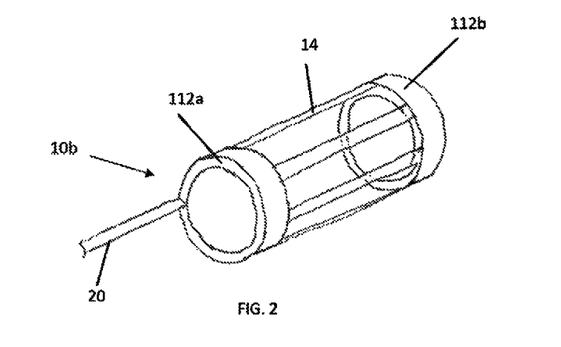
FIG. 2 is a perspective view of a second embodiment of an electrode support positioned on a catheter body.

The electrode support 10b of the second embodiment, shown in FIG. 2, is similar to the first embodiment, but in this case each of proximal and distal inflatable members 112a, 112b has a circumferential border, such as the toroid shown in the drawings, rather than a plurality of spokes. Electrode-carrying struts 14 and, optionally, an additional shaft (like shaft 22), extend between the members 112a, 112b.

Figure 3:
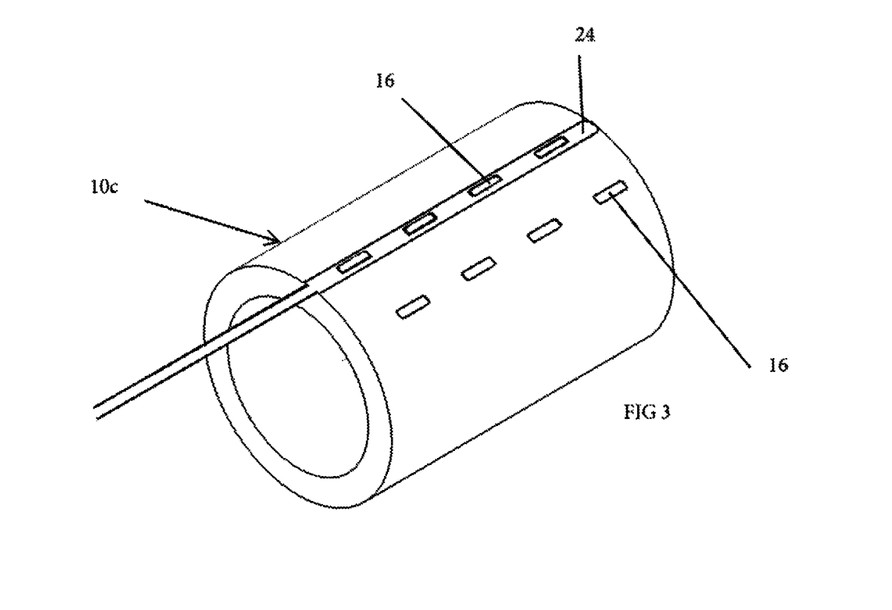
FIG. 3 is a perspective view of a third embodiment of an electrode support positioned on a catheter body.

In the third embodiment shown in FIG. 3, the electrode support 10c is an inflatable tube having arrays of electrodes 16 positioned thereon. The electrodes 16 may be positioned on strips 24 of substrate, such as a flex circuit, attached to the exterior of the balloon and coupled to the catheter (which preferably will be positioned along the vessel wall during use). Alternatively, the electrodes may be directly attached to the inflatable member, such as through printing or through use of an adhesive. See the longitudinal array of electrodes on the right hand side of FIG. 3.

It is desirable to configure the tubular support 10c such that when it is inflated, the material defining its lumen does not radially expand into the lumen where it would reduce the diameter of the lumen and potentially obstruct blood flow. Thus, in the FIG. 3 embodiment, the material defining the lumen of the inflatable tubular support 10c may be rigid or inelastic (e.g. nylon) so as to prevent or limit radial expansion. On the other hand, the exterior surface (defining the outer circumference of the tubular support 10c) may be formed of a more flexible or expandable material so as to allow radial expansion of the outer diameter, allowing the electrodes to make secure contact with the surrounding vessel wall. Exemplary materials for the exterior of the tubular support 10c include silicone or urethane.

Figure 4A:
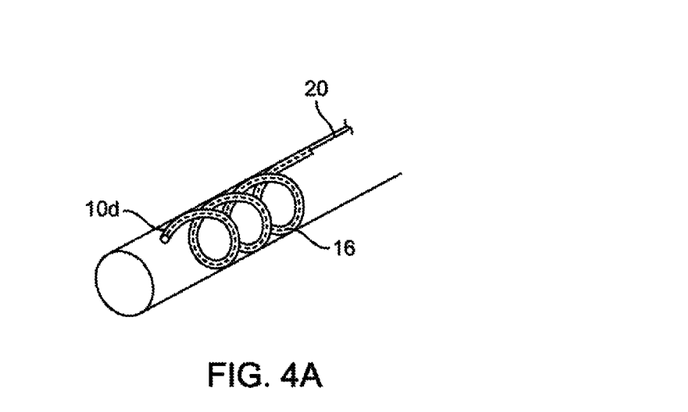
FIG. 4A schematically shows a fourth embodiment of an electrode support positioned within a blood vessel.
Figure 4B:
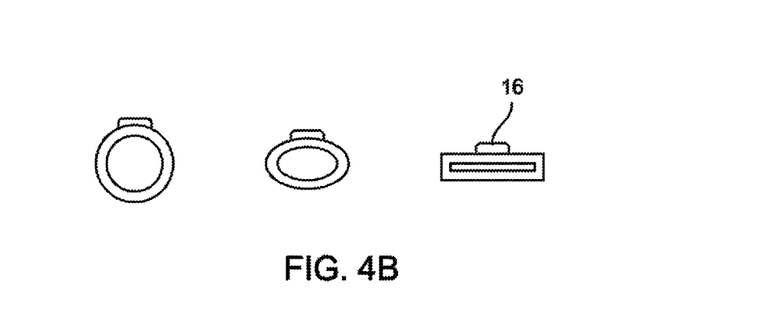
FIG. 4B shows three cross-section views, each showing an exemplary cross-section for the electrode support of FIG. 4A.

Support 10d of the fourth embodiment, shown in FIG. 4A, is an inflatable spiral member having the electrodes disposed on the spiral. The catheter 20 upon which the support 10d is positioned may be arranged to extend along the wall of the vessel as shown, or centrally within the lumen (offset from the vessel wall). Exemplary cross-sectional shapes for the support 10d are shown in FIG. 4D.

As described above, rigid or inelastic material such as nylon may be used for the inflatable member to limit changes in shape/dimensions of the spiral member. In this variation, the user might be provided with a collection of spiral members, each having a different radial diameter, allowing the practitioner to select a size most suitable for the anatomy of a particular patient.

Figure 5A:
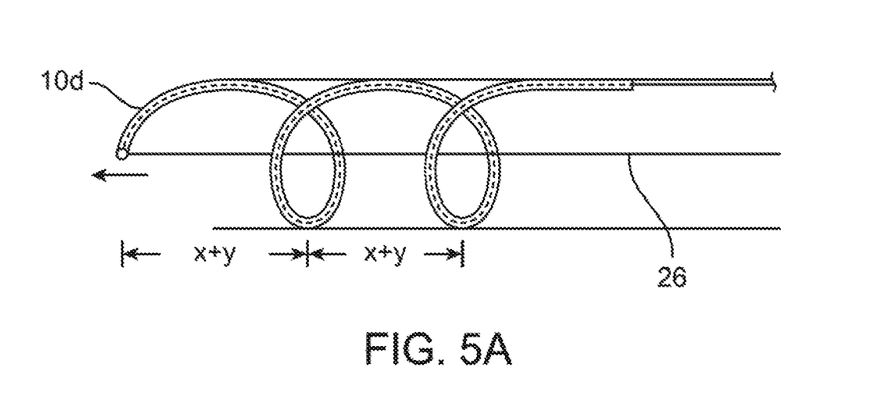
FIG. 5A is a side view schematically illustrating the electrode support of FIG. 4A in an elongated position.
Figure 5B:
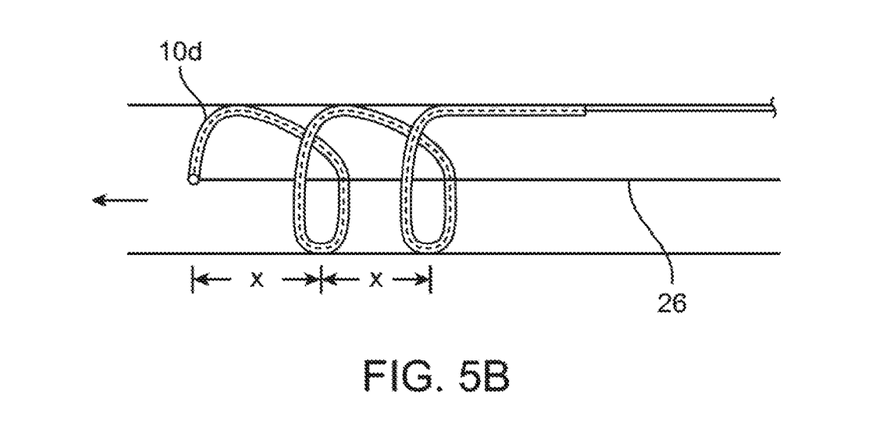
FIG. 5B is similar to FIG. 5A but shows the support prior to longitudinal expansion.

Alternatively, a more flexible or elastic balloon material (silicone, urethane) might be used to allow the user to adjust the longitudinal spacing of the windings of the spiral using manual control. In this embodiment, a mandrel 26 (see FIG. 5B) attached at a distal portion of the spiral may be moved distally or proximally to change the spacing between the windings and to thus adjust longitudinal electrode spacing. When the mandrel is pushed in a distal direction, it longitudinally stretches the balloon, increasing the distance between the windings as illustrated in FIG. 5A. A change in the longitudinal spacing of the electrodes may be desired to optimize electrode spacing or electrode location so as to optimize trans-vessel stimulation of a nerve.

Figure 6:
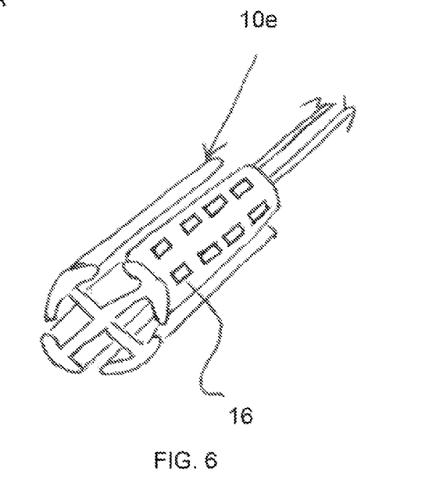
FIG. 6 is a perspective view of a fifth embodiment of an electrode support positioned on a catheter body.
Figure 7A:
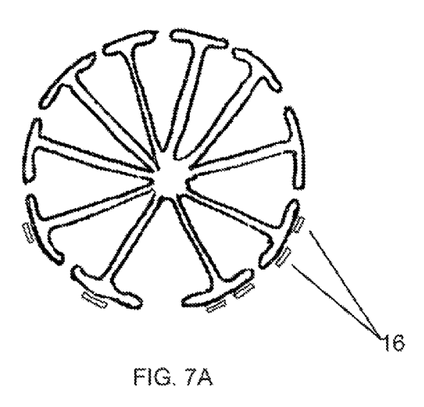
FIGS. 7A and 7B are two cross-section views, each showing an exemplary cross-section for the electrode support of FIG. 6.
Figure 7B:
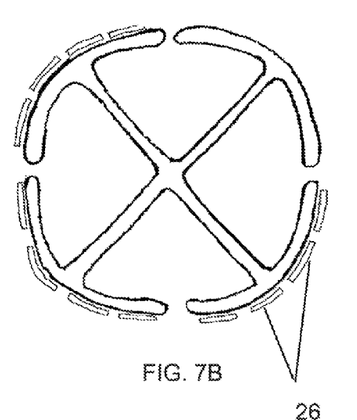

Referring to FIG. 6, support 10e is an inflatable support comprised of a plurality of radially- and longitudinally-extending strut members 28, each supporting an elongate circumferential wing 30. Electrodes 16 are disposed on the wings 30 as shown. FIGS. 7A and 7B show exemplary cross-section views of the support 10e. FIG. 7A illustrates the use of ten strut members, whereas FIG. 7B shows four strut members to utilize a smaller amount of material within the vessel lumen. As shown, the circumferential dimensions of the wings 300 may be selected to accommodate one (FIG. 7A, left side), two (FIG. 7A, right side), or more (FIG. 7B) circumferential arrangements of electrodes 16. In a variation of the FIG. 6 embodiment, the longitudinal strut members 28 may be replaced by non-inflatable supports, such as wires or struts made of nitinol or other material, to support the inflatable wings 30. Such an arrangement allows more diametric flexibility to the array when deployed.

Figure 8A:
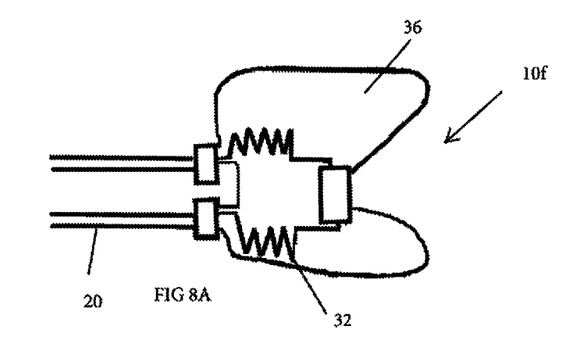
FIGS. 8A and 8C are side views of a sixth embodiment prior to longitudinal expansion of its inflatable member.
Figure 8B:
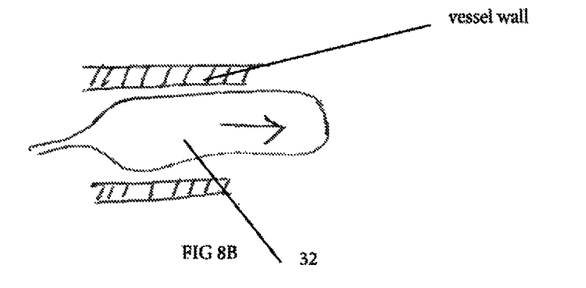
FIGS. 8B and 8D show the sixth embodiment following longitudinal expansion of its inflatable member.
Figure 8C:
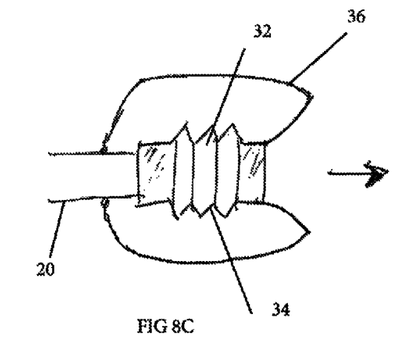
Figure 8D:
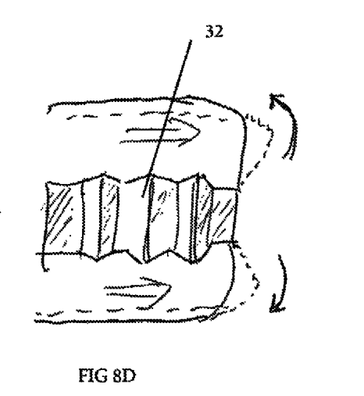

FIGS. 8A through 8D illustrate an electrode support 10f which is similar to the FIG. 1A embodiment in that an inflatable member is used to bias electrodes that are carried by struts. Referring to FIGS. 8A and 8C, inflatable member 32 has a proximal end disposed on the end of catheter 20. The member 32 is configured such that when inflated with inflation medium, it expands in a longitudinally distal direction. In the illustrated example, the member 32 includes bellows 34 that are folded when the member 32 is in the uninflated stated, and that unfold when the member is inflated, thus causing it to lengthen in a distal direction as shown in FIGS. 8B and 8D.

Electrode-carrying struts 36 each have a proximal portion fixed to the catheter 30 or to another member in a fixed position proximal to the inflatable member 32. The distal portion of each strut 36 is connected to a distal portion of the inflatable member. Electrodes are positioned on the struts 36 (e.g. on the generally horizontal sections shown in the drawings). The cabling/wiring for the struts may extend through the interior or along the exterior of the catheter.

When the inflatable member 32 is inflated, its longitudinal expansion functions like a piston, driving the distal ends of the struts in a distal direction and causing them to swing outwardly as indicated in FIG. 8D, thus biasing the electrodes against the vessel wall.

Figure 9A:
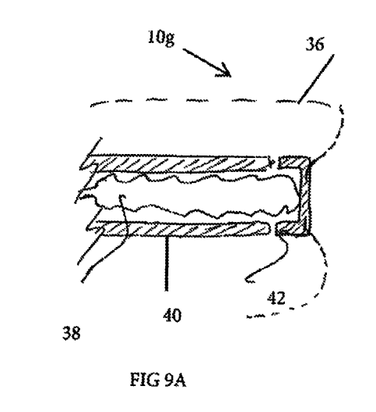
FIG. 9A is a side view of a seventh embodiment prior to longitudinal expansion of its inflatable member.
Figure 9B:
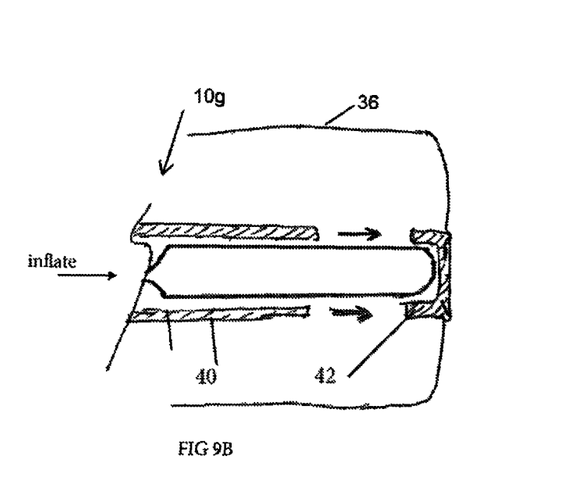
FIG. 9B shows the seventh embodiment following longitudinal expansion of its inflatable member.

The electrode support 10g shown in FIGS. 9A and 9B likewise uses a longitudinally-expandable balloon for piston-like action against the distal portions of the struts 36. In this embodiment, a balloon 38 (which need not have bellows features of the type described above) is contained within a chamber 40 having a distal element or cap 42. Inflation of the balloon causes the balloon to expand distally, since the proximal wall and sidewalls of the chamber prevent the balloon from expanding proximally or radially beyond their boundaries. Distal expansion of the balloon advances cap in a distal, longitudinal direction, causing the distal portions of the struts to swing or pivot outwardly as described above.

Figure 10A:
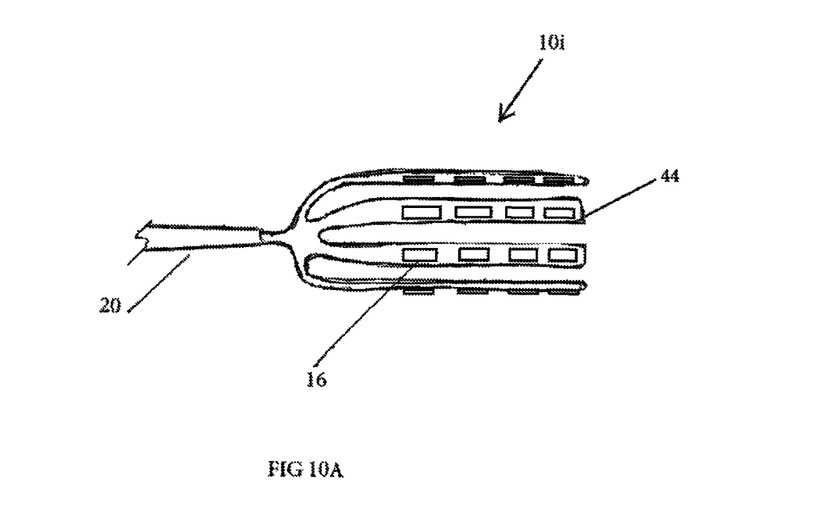
FIG. 10A is a side elevation view of an eighth embodiment of an electrode support.
Figure 10B:
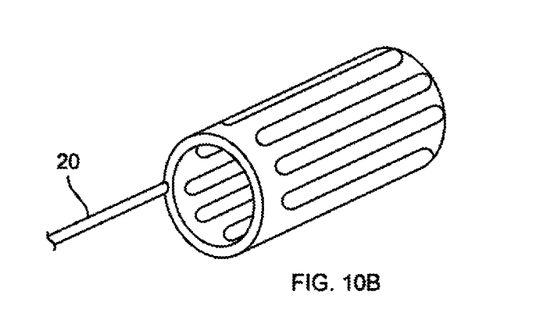
FIG. 10B is a perspective view of a slightly-modified design of the eighth embodiment.
Figure 10C:
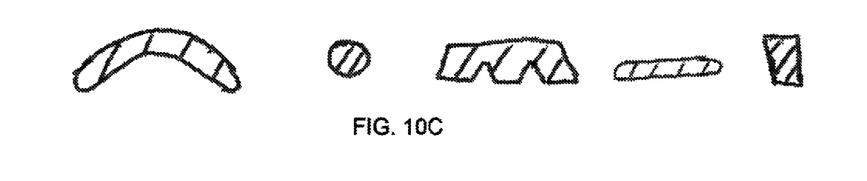
FIG. 10C shows exemplary cross-sectional shapes for the eighth embodiment.

FIG. 10A shows an electrode support 10i comprised of an inflatable member that includes a plurality of longitudinally extending arms 44, with each arm having a distal free end. The catheter shaft 20 may be disposed along the longitudinal axis of the member 10i as shown in FIG. 10A (so it will extend centrally within the vascular lumen—offset from the vessel walls), or it may be laterally offset from the longitudinal axis such that it lies along the vessel wall as shown in FIG. 10B. The cross-sectional shape of the arms may be selected based on desired parameters, such as optimally accommodating the electrodes, minimizing the overall cross-sectional area of the device within the lumen, and/or improving the stiffness or strength of the arms. Exemplary arm cross-sections are shown in FIG. 10C.

It should be recognized that a number of variations of the above-identified embodiments will be obvious to one of ordinary skill in the art in view of the foregoing description. Moreover, it is contemplated that aspects of the various disclosed embodiments may be combined to produce further embodiments. Accordingly, the invention is not to be limited by those specific embodiments and methods of the present invention shown and described herein. Rather, the scope of the invention is to be defined by the following claims and their equivalents.

All prior patents and applications referred to herein, including for purposes of priority, are incorporated by reference for all purposes.

We claim:

1. An intravascular catheter positionable within a blood vessel having a wall, comprising:
    a catheter body;
    a support at a distal end of the catheter body, the support including proximal and distal inflatable members and at least one non-inflatable electrode-carrying strut having a proximal end connected to the proximal inflatable member and a distal end connected to the distal inflatable member;
    a plurality of neuromodulation electrodes energizable to capture target nerve fibers external to the blood vessel wall, the electrode carrying strut having at least one of the plurality of neuromodulation electrodes such that inflation of the proximal and distal inflatable members biases
    at least a portion of the plurality of electrodes into contact with the blood vessel wall.

2. The catheter of claim 1, wherein:
    the support includes a plurality of non-inflatable electrode-carrying struts, each of said electrode-carrying struts having a proximal end connected to the proximal inflatable member and a distal end connected to the distal inflatable member, each electrode carrying strut having at least one of the neuromodulation electrodes disposed thereon.

3. The catheter of claim 2, wherein at least one of the proximal and distal inflatable members includes a plurality of inflatable radially-extending spokes.

4. The catheter of claim 2, wherein at least one of the proximal and distal inflatable members is, in the inflated position, an annular member.

5. The catheter of claim 2, further including a shaft extending longitudinally between the proximal and distal inflatable members.

6. The catheter of claim 5, wherein the shaft is an inflatable shaft.

7. The catheter of claim 1, wherein the electrode-carrying strut is a shape set element.

8. The catheter of claim 1, wherein the electrode-carrying strut is a shape memory element.

\* \* \* \* \*